(12) United States Patent
Huang et al.

(10) Patent No.: US 10,820,729 B2
(45) Date of Patent: Nov. 3, 2020

(54) KIND OF MULTIPURPOSE PILLOW

(71) Applicant: CHENG-DU SIFU HYDRAULIC EQUIPMENT CO., LTD, Sichuan (CN)

(72) Inventors: Yong Huang, Chengdu (CN); Musen Xie, Chengdu (CN); Shuangxi Zhang, Chengdu (CN)

(73) Assignee: CHENGDU SIFU HYDRAULIC EQUIPMENT CO., LTD, Sichuan (CN)

( * ) Notice: Subject to any disclaimer, the term of this patent is extended or adjusted under 35 U.S.C. 154(b) by 389 days.

(21) Appl. No.: 15/742,959

(22) PCT Filed: Sep. 2, 2015

(86) PCT No.: PCT/CN2015/088860
§ 371 (c)(1),
(2) Date: Jan. 9, 2018

(87) PCT Pub. No.: WO2017/008381
PCT Pub. Date: Jan. 19, 2017

(65) Prior Publication Data
US 2019/0082867 A1 Mar. 21, 2019

(30) Foreign Application Priority Data
Jul. 14, 2015 (CN) .......................... 2015 1 0412527

(51) Int. Cl.
*A47G 9/10* (2006.01)
*A61N 2/00* (2006.01)
(Continued)

(52) U.S. Cl.
CPC .............. *A47G 9/1045* (2013.01); *A47G 9/10* (2013.01); *A47G 9/109* (2013.01); *A47G 9/1036* (2013.01);
(Continued)

(58) Field of Classification Search
CPC ........ A47G 9/10; A47G 9/1036; A47G 9/109; A47G 2009/01; A47G 2009/004;
(Continued)

(56) References Cited

U.S. PATENT DOCUMENTS 2,917,046 A * 12/1959 Fairbanks ........... A61M 16/109
128/202.18
2,943,621 A * 7/1960 Phillips .............. A61H 23/0218
601/57
(Continued)

FOREIGN PATENT DOCUMENTS

CN 202365440 U * 8/2012
CN 202365440 U 8/2012
(Continued)

*Primary Examiner* — David R Hare
*Assistant Examiner* — Alexis Felix Lopez
(74) *Attorney, Agent, or Firm* — Alan D. Kamrath; Karin L. Williams; Mayer & Williams PC

(57) ABSTRACT

A multifunctional pillow, which is related to the field of medical healthcare, comprising: a cervical curve standard pillow (1), a control board (2), a magnetic therapy massage bar (11), a heating strip (12), an intermediate-frequency electrotherapy bar (13), an ultrasound therapy head (21), a negative ion generator (22), a music player (23), a health and sleep-aiding mask (24), and a microcontroller (25). The magnetic therapy massage bar (11), the heating strip (12), the intermediate-frequency electrotherapy bar (13) are arranged within the cervical curve standard pillow (1). The negative ion generator (22), the music player (23), and the microcontroller (25) are arranged on the control board (2). The multifunctional pillow relies on a cervical curve standard, effectively restores a distended cervical spine, and allows people to fall asleep as quickly as possible, to relax the head, and to restore physical strength in a quality sleep environment.

8 Claims, 1 Drawing Sheet

(51) Int. Cl.
*A61N 1/00* (2006.01)
*A47G 9/00* (2006.01)
*A61N 1/04* (2006.01)
*A61N 1/36* (2006.01)

(52) U.S. Cl.
CPC ............... *A61N 1/00* (2013.01); *A61N 2/00* (2013.01); *A47G 2009/001* (2013.01); *A47G 2009/004* (2013.01); *A47G 2009/006* (2013.01); *A61N 1/0404* (2013.01); *A61N 1/36014* (2013.01)

(58) Field of Classification Search
CPC .... A47G 2009/006; A61N 1/00; A61N 1/025; A61N 1/0404; A61N 1/36014; A61N 2/00; A61N 2/002
See application file for complete search history.

(56) References Cited

U.S. PATENT DOCUMENTS

| | | | | |
|---|---|---|---|---|
| 3,103,219 | A * | 9/1963 | Chadner | A61F 7/007 607/109 |
| 3,648,469 | A * | 3/1972 | Chapman | A47G 9/1036 62/3.5 |
| 4,018,218 | A * | 4/1977 | Carlson | A61N 1/36046 600/26 |
| 4,066,072 | A * | 1/1978 | Cummins | A61B 5/6892 601/15 |
| 5,361,437 | A * | 11/1994 | Zhu | A61H 23/0218 5/639 |
| 5,479,667 | A * | 1/1996 | Nelson | A47G 9/10 5/636 |
| 5,566,685 | A * | 10/1996 | Litovitz | A61N 1/16 128/898 |
| 6,042,531 | A * | 3/2000 | Holcomb | A61N 2/00 600/13 |
| 6,050,265 | A * | 4/2000 | Richardson | A61G 7/065 128/845 |
| 6,109,256 | A * | 8/2000 | Sardi | A47C 7/748 126/204 |
| 6,189,487 | B1 * | 2/2001 | Owen | A01K 1/0157 119/28.5 |
| 6,236,621 | B1 * | 5/2001 | Schettino | A47G 9/1045 368/10 |
| 6,256,818 | B1 * | 7/2001 | Hughes | A47G 9/1036 5/421 |
| 6,668,407 | B1 * | 12/2003 | Reitzel | A47C 1/14 5/639 |
| 7,158,834 | B2 * | 1/2007 | Paul, Jr. | A61N 1/326 607/141 |
| 7,484,255 | B2 * | 2/2009 | Ho | A61F 5/56 5/636 |
| 7,676,870 | B2 * | 3/2010 | Chen | A61F 5/56 5/640 |
| 8,468,628 | B1 * | 6/2013 | Cheng | A47G 9/007 5/632 |
| 8,492,680 | B2 * | 7/2013 | Ohashi | B60N 2/5685 219/202 |
| 8,661,586 | B2 * | 3/2014 | Melcher | A61G 7/07 5/630 |
| 8,719,981 | B2 * | 5/2014 | Jaskot | A47G 9/10 5/636 |
| 9,586,021 | B2 * | 3/2017 | Franceschetti | A61B 5/4266 |
| 9,968,797 | B2 * | 5/2018 | Sham | A61F 7/007 |
| 2003/0056281 | A1 * | 3/2003 | Hasegawa | A61F 7/02 2/428 |
| 2007/0061975 | A1 * | 3/2007 | Hernandez | A47G 9/1045 5/639 |
| 2007/0124862 | A1 * | 6/2007 | Beyda | H04R 5/023 5/639 |
| 2007/0253591 | A1 * | 11/2007 | Popilek | H04R 5/023 381/388 |
| 2009/0089931 | A1 * | 4/2009 | Vandenbelt | A47G 9/1045 5/639 |
| 2009/0094750 | A1 * | 4/2009 | Oguma | A61F 5/56 5/636 |
| 2009/0211030 | A1 * | 8/2009 | Norstrem | A47G 9/10 5/640 |
| 2010/0145167 | A1 * | 6/2010 | Im | A47G 9/1045 600/301 |
| 2011/0061661 | A1 * | 3/2011 | Hayes | A47G 9/1045 128/845 |
| 2011/0219547 | A1 * | 9/2011 | Ryan | A47G 9/10 5/652 |
| 2011/0275966 | A1 * | 11/2011 | Alkhattaf | A61F 7/08 601/49 |
| 2012/0029322 | A1 * | 2/2012 | Wartena | A61B 5/0476 600/301 |
| 2012/0073057 | A1 * | 3/2012 | Sramek | A47G 9/109 5/645 |
| 2012/0079660 | A1 * | 4/2012 | Chen | A47G 9/10 5/644 |
| 2012/0117733 | A1 * | 5/2012 | Chen | A47G 9/1009 5/652.1 |
| 2012/0142999 | A1 * | 6/2012 | Albu | A61B 5/1118 600/26 |
| 2013/0043988 | A1 * | 2/2013 | Bruno | A47G 9/0253 340/407.1 |
| 2013/0085551 | A1 * | 4/2013 | Bachinski | A61N 1/36014 607/59 |
| 2013/0218244 | A1 * | 8/2013 | Iwanami | A47G 9/1036 607/104 |
| 2013/0228392 | A1 * | 9/2013 | Iwata | H04R 1/28 181/148 |
| 2014/0059774 | A1 * | 3/2014 | Lv | A47G 9/10 5/655 |
| 2014/0083434 | A1 * | 3/2014 | Groteke | A61N 1/0476 128/845 |
| 2014/0296747 | A1 * | 10/2014 | Herrnsdorf | A61F 5/56 600/586 |
| 2014/0310878 | A1 * | 10/2014 | Herrnsdorf | A61F 5/56 5/640 |
| 2014/0366273 | A1 * | 12/2014 | Davis, II | G04G 13/02 5/639 |
| 2015/0000042 | A1 * | 1/2015 | Randall | A47G 9/10 5/655.4 |
| 2015/0342377 | A1 * | 12/2015 | Hall | A47G 9/1045 345/156 |
| 2015/0374149 | A1 * | 12/2015 | Wong | A47G 9/1045 5/636 |
| 2016/0324720 | A1 * | 11/2016 | Lear | A61F 7/007 |
| 2017/0013979 | A1 * | 1/2017 | Kim | A47G 9/1045 |
| 2019/0082867 | A1 * | 3/2019 | Huang | A47G 9/10 |
| 2019/0388020 | A1 * | 12/2019 | Stauch | A61B 5/04004 |

FOREIGN PATENT DOCUMENTS

| | | | |
|---|---|---|---|
| CN | 103222764 A | * | 7/2013 |
| CN | 103222764 A | | 7/2013 |
| CN | 107536353 A | * | 1/2018 |
| JP | 2003235919 A | * | 8/2003 |
| KR | 20040003400 A | * | 1/2004 |
| KR | 20040003400 A | | 1/2004 |
| KR | 100992562 B1 | * | 11/2010 |
| KR | 20130005802 A | * | 1/2013 |

* cited by examiner

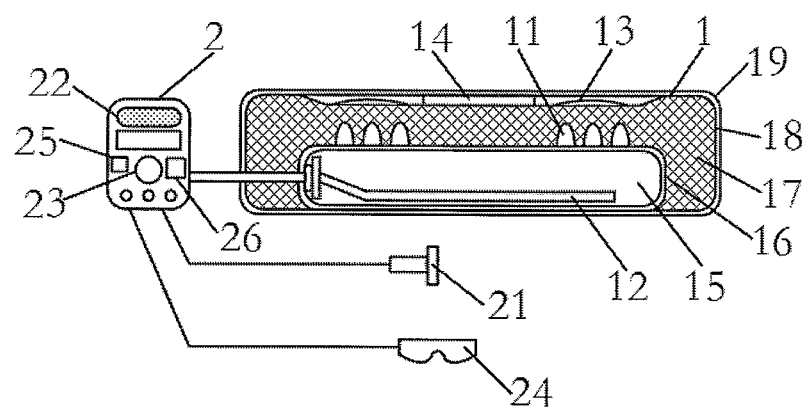

KIND OF MULTIPURPOSE PILLOW

FIELD OF THE INVENTION

This invention refers to a kind of multipurpose pillow in medical health care field.

DESCRIPTION OF THE RELATED ART

Pillow is tool which people rest their head on when they are in bed. It is widely believed that heath care pillow can provide comfort when people sleep. Modern medical research finds that human's spine looks like a straight line from the front but like a long curve with four small physiological curves from the side. Pillow needs to be used when because it can protect neck's normal psychological bending, and maintain people's normal psychological activities when they are asleep.

The cervical spondylopathy is not only a common disease frequently occurring but also an occupational disease white collar workers suffer. Many cervical health care pillows developed by existing technologies are intended for treatment and prevention of cervical diseases, such as TCM health care pillow and magnetic health care pillow. These pillows are expensive but unable to treat cervical diseases effectively.

BRIEF SUMMARY OF THE INVENTION

This invention provides a multipurpose pillow which can address the problem that health care pillows developed by existing technologies are expensive but unable to treat cervical diseases effectively.

The aims of this invention are attained by following solutions:

The multipurpose pillow is composed of standard cervical flexure pillow (1), control panel (2), magnetic massage bar (11), heating band (12), middle-frequency electro-therapeutic bar (13), ultrasonic treatment head (21), anion generator (22), music player (23), hypnosis cover (24) and micro-controller (25). The magnetic massage bar (11), heating band (12), and middle-frequency electro-therapeutic bar (13) are located within standard cervical flexure pillow. The anion generator (22), music player (23), and hypnosis cover (24) are situated on control panel (2). The heating band (12), ultrasonic treatment head (21), and hypnosis cover (24) are connected with control panel (2) through wire. The micro-controller (25) is linked to heating band (12), middle-frequency electro-therapeutic bar (13), ultrasonic treatment head (21), anion generator (22), music player (23) and hypnosis cover (24).

The technical results of this invention are as follows:

The cervical vertebra will be restored from deformation according to cervical flexure standards.

High-quality sleeping environment can be also provided so that people can fall asleep very soon with their head relaxed to resume physical strength.

BRIEF DESCRIPTION OF THE SEVERAL VIEWS OF THE DRAWING(S)

To clearly explain the implementation case of this invention or technical solutions offered by existing technologies, a brief introduction will be given to the figures of the implementation case. It is obvious that the figures below are only some implementation cases of this invention. The ordinary technicians in this domain may derive other figures from these figures without paying creative efforts.

FIG. 1: Structural diagram of the multipurpose pillow in the implementation case of this invention.

DETAILED DESCRIPTION OF THE INVENTION

Further explanation on this invention is made in combination with figures and specific implementation modes so that the aims, features and advantages of this invention can be understood more clearly.

As shown by FIG. 1, the multipurpose pillow is composed of standard cervical flexure pillow (1), control panel (2), magnetic massage bar (11), heating band (12), middle-frequency electro-therapeutic bar (13), ultrasonic treatment head (21), anion generator (22), music player (23), hypnosis cover (24) and micro-controller (25). The magnetic massage bar (11), heating band (12), and middle-frequency electro-therapeutic bar (13) are located within standard cervical flexure pillow. The anion generator (22), music player (23), and hypnosis cover (24) are situated on control panel (2). The heating band (12), ultrasonic treatment head (21), and hypnosis cover (24) are connected with control panel (2) through wire. The micro-controller (25) is linked to heating band (12), middle-frequency electro-therapeutic bar (13), ultrasonic treatment head (21), anion generator (22), music player (23) and hypnosis cover (24).

The standard cervical flexure pillow (1) is comprised of hard pillow body (15), protection cover (16), comfortable layer (17), shaper (18) and pillowcase (19). The middle of the hard pillow body is designed as a cervical flexure surface, with its edge being a narrow-to-wide draft surface. The cervical flexure surface can be customized according to different standards. For example, For adult: height 1.41 m~1.58 m, degree of flexure 41 mm~63 mm; height 1.58 m~1.75 m, degree of flexure 48 mm~70 mm; height 1.75 m~1.92 m, degree of flexure 55 mm~77 mm For children: height 0.9 m~1.07 m, degree of flexure 20 mm~42 mm; height 1.07 m~1.24 m, degree of flexure 27 mm~49 mm; height 1.24 m~1.41 m, degree of flexure 34 mm~56 mm The hard pillow body (15) is made of metal or non-metal materials.

The inner part of protection cover (16) matches up with outer part of the hard pillow body (15); the inner framework of the comfortable layer (17) fits in with the outer part of the protection cover; the inner shape of the shaper (18) consists with the outer part of the comfortable layer (17) and the bottom of the hard pillow body (15); the inner framework of the pillowcase (19) coincides with the outer part of the shaper (18) in size.

The comfortable layer (17) is made of the viscoelastic foam or polyester wadding slowly rebounding. The pillowcase (19) is made of the anti-mite bamboo fiber or velvet.

The magnetic massage bar (11) is equipped with several rounded convex heads which have rounded magnetic blocks, and the magnetic massage bar (11) is made of the editable silica gel The heating band (12) is made of the insulated and flame-resistant glass fiber and heating wire. The middle-frequency electro-therapeutic bar (13) is furnished with middle-frequency electrode and made of editable silica gel. The ultrasonic treatment head (21) consists of ultrasonic generator circuit and transducer. The anion generator (22) is made up of high-pressure anion generating circuit sealed by epoxy resin and the long-life carbon-fiber emitter.

The multipurpose pillow is also composed of the test sensor (14) and the network module (26) that can monitor and record human's sleep quality. The test sensor is located on the surface of the standard cervical flexure surface, which can monitor the sleep quality. The network module (26) is installed within the control panel (2) and connected with local area network. The micro-controller (25) is linked to the test sensor (14) and the network module (26). The test sensor (14) tests the movements of brain during sleep, which can show whether users are in deep sleep and whether they toss and turn. Then, analysis on the data processed by system processor can be made to ascertain when users fall asleep, when they wake up, when they are in deep sleep and in light sleep, and whether they sleep in a right posture. Afterwards, these information can be uploaded to server or transmitted to mobile terminal through network module.

The control panel (2) is connected with reliable power source and AC power source of external computer through cable.

This invention is aimed at promoting recovery of fixed vertebra's ligament and muscle tone. Besides standard cervical flexure pillow, there is also the acupoint's magnetic massage bar (11) characterized by sedation, analgesia, detumescence, anti-inflammation, and antihypertension; the heating band (12) which can generate heat to promote metabolism of local tissues, edema absorption, and trauma repair as well as attain the goals of detumescence, anti-inflammation, spasmolysis, and sedation; the middle-frequency electro-therapeutic bar (13) which has the functions such as analgesia, detumescence, anti-inflammation, improvements in local blood circulation, stimulation of nerve muscle, and muscle building or relaxing; the ultrasonic treatment head (21) which can soften tissues, improve permeability, metabolism and blood circulation, relieve pain and muscle spasms; the anion generator (22) which has various functions like electrostatic dust collection, air purification, improvements in pulmonary function, myocardial function and viability, sedation, hypnosis, metabolism promoting, enhancement of disease resistance, and sterilization; the music player (23) for relaxation, emotional release, emotional adjustments, tension easing, and replacement of tense mood with pleasant thoughts to improve sleep quality; the hypnosis cover (24) that can help to attain mental tranquility, block out the light to improve sleep quality, and get rid of fatigue; and the micro-controller (25) that controls heating band, middle-frequency electro-therapeutic bar, ultrasonic treatment head, anion generator, music player and hypnosis cover.

This invention, a standard cervical flexure sleep system developed based on the treatment principles above, has two functions:

1 The cervical vertebra will be restored from deformation according to cervical flexure standards.

2 High-quality sleeping environment can be also provided so that people can fall asleep very soon with their head relaxed to resume physical strength.

Above is a detailed explanation on this invention. Specific case has been used to describe the principle and implementation mode of this invention. The explanation on the implementation case above is only aimed at helping people understand the methods and key thoughts of this invention. Meanwhile, ordinary technicians in this field may make changes to the implementation modes and applicable scopes according to the ideas of this invention. To sum up, the contents of this specification shall not be construed as the constraints over this invention.

The invention claimed is:

1. A multipurpose pillow comprising: a standard cervical flexure pillow, a control panel, a magnetic massage bar, a heating band, a middle-frequency electro-therapeutic bar, an ultrasonic treatment head, an anion generator, a music player, a hypnosis cover and a micro-controller;
    wherein the magnetic massage bar, the heating band, and the middle-frequency electro-therapeutic bar are located within standard cervical flexure pillow;
    wherein the anion generator, the music player, and the hypnosis cover are situated on the control panel;
    wherein the micro-controller is linked to the heating band, the middle-frequency electro-therapeutic bar, the ultrasonic treatment head, the anion generator, the music player and the hypnosis cover;
    wherein the standard cervical pillow includes a hard pillow body, a protection cover, a comfortable layer, a shaper and a pillowcase;
    wherein a middle of the hard pillow body has a cervical flexure surface, an edge of the hard pillow body is a narrow-to-wide draft surface, and the cervical flexure surface of the hard pillow is adjustably set based on using requirements.

2. The multipurpose pillow as claimed in claim 1, wherein the hard pillow body (15) is made of metal or non-metal materials.

3. The multipurpose pillow as claimed in claim 1, wherein an inner part of the protection cover matches up with an outer part of the hard pillow body; an inner framework of the comfortable layer fits in with an outer part of the protection cover; an inner shape of the shaper consists with an outer part of the comfortable layer and a bottom of the hard pillow body; an inner framework of the pillowcase coincides with an outer part of the shaper in a size.

4. The multipurpose pillow as claimed in claim 1, wherein the comfortable layer is made of viscoelastic foam or polyester wadding slowly rebounding; the pillowcase is made of anti-mite bamboo fiber or velvet.

5. The multipurpose pillow as claimed in claim 1, the magnetic massage bar is equipped with several rounded convex heads which have rounded magnetic blocks, and the magnetic massage bar is made of editable silica gel.

6. The multipurpose pillow as claimed in claim 1, the heating band is made of insulated and flame-resistant glass fiber and heating wire; the middle-frequency electro-therapeutic bar is furnished with middle-frequency electrode and made of editable silica gel; the ultrasonic treatment head has ultrasonic generator circuit and transducer; the anion generator is made up of high-pressure anion generating circuit sealed by epoxy resin and the long-life carbon-fiber emitter.

7. The multipurpose pillow as claimed in claim 1 further comprising a test sensor and a network module; wherein the test sensor is located on a standard cervical flexure surface to monitor sleep quality; the network module is installed within the control panel and connected with a local area network; the micro-controller is linked to the test sensor and the network module.

8. The multipurpose pillow as claimed in claim 1, the control panel is connected with a power source and an AC power source of an external computer through a cable.

* * * * *